United States Patent [19]

Wood

[11] Patent Number: 4,907,845
[45] Date of Patent: Mar. 13, 1990

[54] BED PATIENT MONITORING SYSTEM

[76] Inventor: Ron Wood, P.O. Box 35446, Tulsa, Okla. 74153

[73] Assignee: Salonon, SA

[21] Appl. No.: 245,227

[22] Filed: Sep. 16, 1988

[51] Int. Cl.⁴ .............................................. G08B 23/00
[52] U.S. Cl. .................................. 340/573; 200/85 R
[58] Field of Search ....................... 340/573, 666, 686; 200/85 R

[56] References Cited

U.S. PATENT DOCUMENTS

| | | | |
|---|---|---|---|
| 4,179,692 | 12/1979 | Vance | 340/573 |
| 4,228,426 | 10/1980 | Roberts | 340/573 |
| 4,446,345 | 1/1984 | Sheiry | 200/85 R |
| 4,484,043 | 11/1984 | Musick et al. | 200/85 R |
| 4,539,560 | 9/1985 | Fleck et al. | 340/573 |
| 4,633,237 | 12/1986 | Tucknott | 340/573 |
| 4,638,307 | 1/1987 | Swartout | 340/666 |
| 4,658,242 | 4/1987 | Zeder | 340/693 |
| 4,661,664 | 12/1985 | Miller | 340/666 |

Primary Examiner—Reinhard J. Eisenzopf
Assistant Examiner—Maura K. Regan

[57] ABSTRACT

A system is shown for detecting the movements of a patient confined to a bed so as to determine if there is the likihood that the patient is trying to leave the bed. A sensor is arranged to be placed under the mattress of a bed next to the frame and is totally sealed from the intrusion of contaminants so that it is not necessary to discard the sensor after a patient is discharged. The sensor utilizes ribbon switches sandwiched in assembly between stiff plexiglas plates. The assembly is sealed in a bag that holds the parts in assembly while permitting relative movement in all directions. The alarm system is arranged so that if the sensor detects undesired patient movement, the regular nurses' call light system is deactivated and an alarm distinguishable therefrom is superimposed on the nurses' call light alarm. In addition, an alarm audible to the patient encourages the patient to return to the desired position on the bed. The system then returns to normal and the alarms cease so that resetting is not necessary. Other alarms are activated at remote locations. A bed rail activated switch is utilized to arm and disarm the system so that if the bed rail is lowered to remove a patient from the bed, the alarms are not activated and when a patient is replaced on the bed and the rail is raised, the system is reactivated.

35 Claims, 2 Drawing Sheets

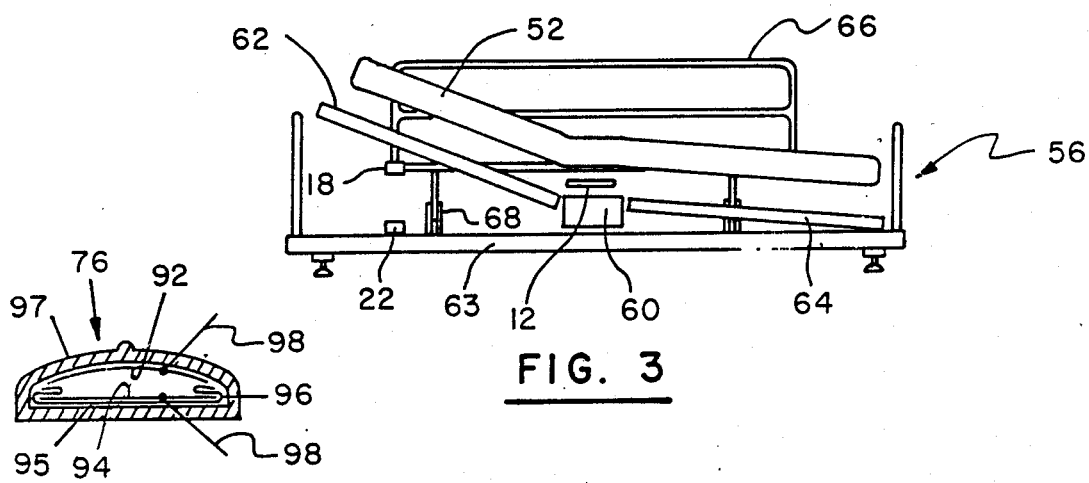
FIG. 3
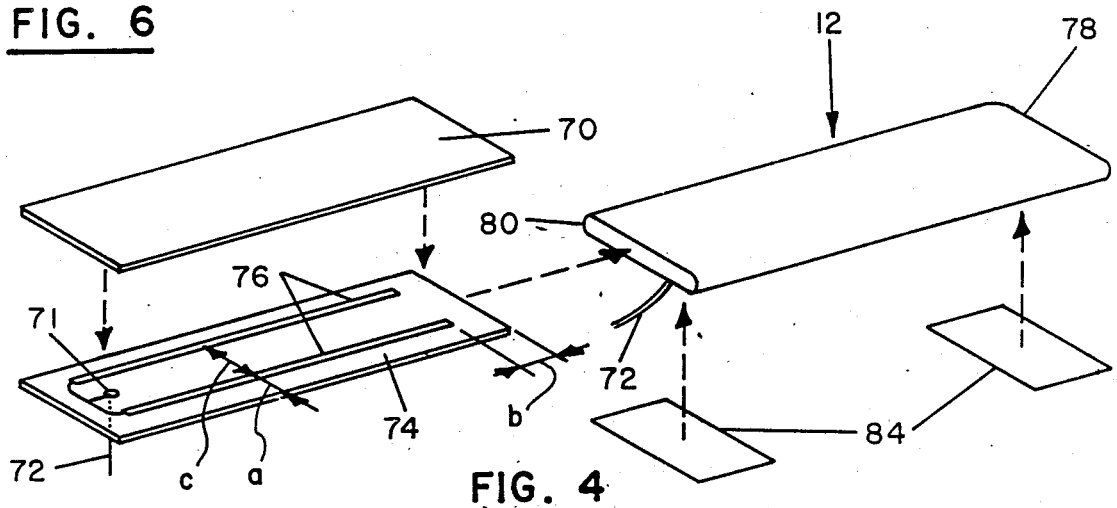
FIG. 6
FIG. 4
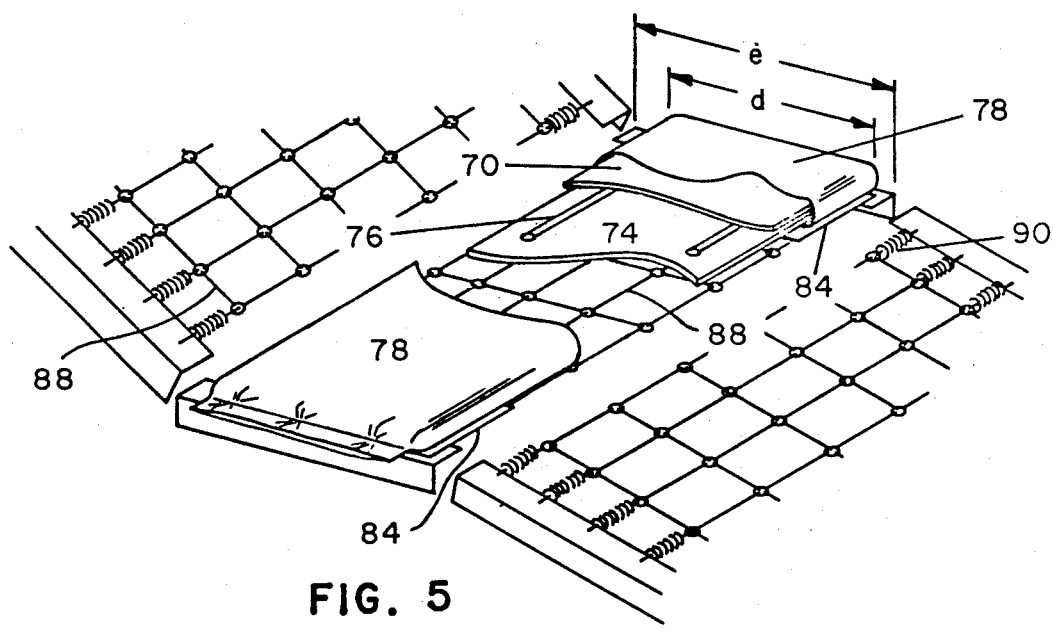
FIG. 5

BED PATIENT MONITORING SYSTEM

BACKGROUND OF THE INVENTION

1. Field of the Invention

This Invention pertains to a bed patient monitoring system and more particularly to a system for detecting the undesired movement of a bed-restricted patient and providing a system of alarms to facilitate returning the patient to a proper position in the bed.

2. Background of the Invention

It is often desirable to restrict patients to their beds and not permit their movement from the bed without supervision of medical personnel or, in many instances, without the direct aid and assistance of such personnel. With the increase of litigation and legal liability in the area of medical care, the consequences of bed-restricted patients getting out of their beds and then being injured, or worsening their condition as a result thereof, is of major economic significance in the health care field. As a result of this and related problems concerning bed-restricted patients, a need has developed to monitor the activity of such patients and to be forewarned that the patient is about to or is trying to leave their bed. One such attempt to solve this problem is set forth in U.S. Pat. No. 4,179,692 issued Dec. 18, 1979, to Dwight A. Vance and entitled "APPARATUS TO INDICATE WHEN A PATIENT HAS EVACUATED A BED OR DEMONSTRATES A RESTLESS CONDITION". The system disclosed in the Vance patent utilizes a variety of switches for detecting patient movement and/or restlessness. The system is arranged to detect the movements of a patient and thereafter try to determine a level of restlessness which when exceeded will indicate that the patient may be getting ready to leave the bed. This and other systems which have attempted to solve this problem have had a variety of shortcomings which are overcome in the present system. If a patient is adjusting themselves in the bed and activates a detecting device which is indicative of an undesirable movement, but in fact the patient is not moving from the bed and resumes a more normal position which would not activate the detecting device, an alarm which may have been activated oftentimes continues to operate even if the patient's activity has ceased.

Other systems do not interface with the nurses' call light which is stationed in the hall over the patient's door and at the nurses' station; or if the systems do interface, they do not differentiate between a patient call and a patient trying to leave a bed, the latter condition normally being a much greater emergency than the former under normal circumstances. On the other hand, some systems require that they be interfaced with the nurses' call station system in order to operate. Many of these systems require rather complex procedures for activating or reactivating the system or for resetting the system if it has been activated. It is desirable to have very simple procedures for activating the system so that doctors, nurses, orderlies or the like, or even visitors or family members who are not familiar with the system, will not inadvertently set off the alarm or if they have deactivated the system in order to move a patient from the bed, forget or be prone to avoid activating or resetting the system because of the complexity of the system or because of forgetfulness. It is also important that any alarm device at a remote location have some means for identifying the discreet room number that houses the patient making an undesirable move. Another problem with such prior systems is that a malfunction in the system is not readily detectable and thus the system may not be working and this not be known to the health care staff. Yet another problem is that of the patient having some way to intentionally or unintentionally either disarm the system or trigger a false alarm. In some systems, once an alarm is set off, each bed must be reset.

Although it is the express object of the Vance patent, cited above, to provide and signal a level of restlessness, it is more desirable to know if the patient is moving from a desired condition and yet not set off an alarm which must be reset in the patient's room should the condition return to normal. In some systems the sensor is placed directly beneath the patient or beneath a sheet and because it is easily moved by the patient's movements, can be moved out of its desired position and then produce false alarms because the detector is mispositioned rather than the patient. In some systems the detector, when placed on top of the mattress, becomes contaminated by contact with the patient or the patient's body fluids and as a result must be replaced with each new patient or after each occurrence of suspected contamination.

One such detecting device is shown in U.S. Pat. No. 4,565,910; issued on Jan. 21, 1986, to Musick, et al, and entitled "SWITCH APPARATUS RESPONSIVE TO DISTORTION". This device, because of its construction, must be placed under sheets, bedding or the like on top of the mattress and thus is protected from patient contact or body fluid contact by only thin layers of materials. Hospitals using this product routinely require its replacement with a new detector unit with each patient turnover.

It is therefore an object of the present invention to provide a new and improved bed patient monitoring system which will overcome the drawbacks of the prior systems.

SUMMARY OF THE INVENTION

With this and other objects in view, the present system contemplates a bed patient monitoring system including a detection device that when placed beneath the mattress of a bed is sensitive to the weight distribution on top of the mattress to effectively monitor the patient's movement. The detection device is comprised of a ribbon switch array having a pair of parallel conductive strips which are arranged to move away from one another in the absence of pressure and to contact one another under a sufficient pressure source to make an electrical contact. The ribbon switch is sandwiched between a pair of substantially parallel plates that are arranged for relative movement laterally and transversely and are encased in a sealed cover which permits such relative movement between the plates and at the same time holds the plates and the switch in assembly. The cover also seals the assembly from contamination in the environment of the bed patient. The contacts in the ribbon switch are electrically connected to a control device that translates the making and breaking of the contacts into a movement signal for use in operating various alarm devices. One such device includes an already existing nurses' call station alarm system usually consisting of a patient controlled call button positioned at the patient's bedside, a hall light over the patient's door and signal lights and/or audible device at the nurses' station. The control device, when receiving a signal indicative of undesired patient movement, deactivates the regular nurses' call light system and superimposes an alert signal on the nurses' call light system which is distinguishable from the regular signal indicative of the patient calling for help. The alert signal also activates an audible alarm in the patient's room which is designed to encourage the patient to discontinue the undesired movement and to return to the desired position on the bed. If the patient returns to the desired position, the alarm system is automatically reset and the alert signal ceases.

In addition, the movement signal initiates operation of a radio frequency transmitter which sends a discreet signal to a central processing unit at a remote location for identifying the discreet room location of the alert signal and for further transmitting the signal to other remote alarm stations in the system.

In one embodiment of the invention, a switch device is positioned on the bed and movable bed rail so that if the bed rail is lowered, in order to voluntarily move the patient from the bed, the alert system is deactivated and no alarms are initiated. Then, when the patient is returned to the bed and the bed rail is raised to confine the patient, the system is activated to provide an alarm under appropriate circumstances.

BRIEF DESCRIPTION OF THE DRAWINGS

FIG. 3 is a side elevation view of a hospital bed having a bed rail switch for use with the present invention;

FIG. 4 is an exploded perspective view of a movement detection device in accordance with the present invention; and FIG. 5 is a perspective view of the assembled movement detection device of FIG. 4 positioned over a portion of a bed frame; and FIG. 6 is a cross sectional view of a ribbon switch for use in the movement detection device of FIG. 4.

DETAILED DESCRIPTION OF THE PREFERRED EMBODIMENTS

Figure 1:
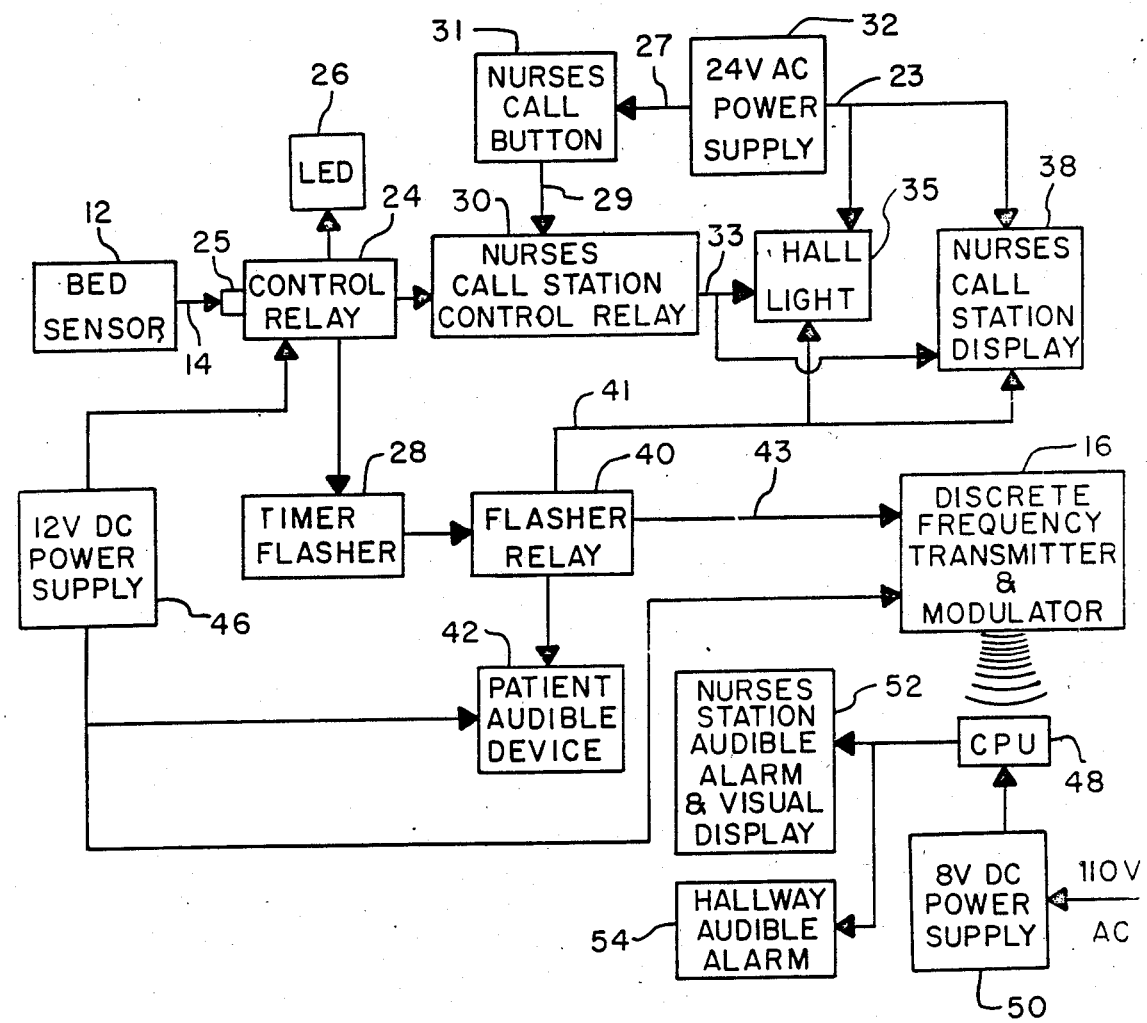
FIG. 1 is a schematic illustration of a circuit diagram showing the bed patient monitoring system of the present invention.

REFERRING first to FIG. 1 of the drawings, a bed patient monitoring system is shown for use in a health care facility having patient rooms and a nurses' station remote from the patient's room. It is readily appreciated that many arrangements of such facilities are possible and that the present invention is described with respect to but a few of such arrangements. A bed sensor 12 which would normally be positioned on or about the patient's bed is shown having a circuit path 14 connected to a control relay 24, the connection is made by means of a male/female quick disconnect microphone jack 25 which has a built-in spring loaded means for closing the circuit path 14 when the male portion of the jack 25 is removed from the female portion of the jack 25 which is shown mounted on the housing of the control relay 24. As will be described later wit reference to FIG. Z of the drawings, a bed rail switch is interposed in the circuit path 14 to provide a functionally unique way to automatically open and close this circuit path 14. A dampening circuit operates in the input to the control relay 24 to provide a momentary delay in the activation of the relay 24 should the bed sensor 12 provide a momentary movement signal. This dampening is provided by a capacitor across the coil of the control relay which gives a time delay of about .2 of a second if the bed sensor switch is opened. As will be described later, the bed sensor includes a ribbon switch which has contacts that are held closed when a patient is properly positioned on the bed. If the patient moves their weight off of the sensor for more than the momentary delay described above, the open contacts of the switch cause the control relay which is normally closed, to open. A first signal path from control relay 24 leads to a light emitting diode 26 which is positioned on the bed or in the patient's room in view of health care workers. A second circuit path from the control relay 24 passes to a flasher timer 28 such as a "555 timer". A third circuit path from the output of control relay 24 passes to a nurses' call station control relay 30.

Most health care facilities have a nurses' call station system already in existence which permits a patient, by pressing a call button 31, to send a signal to a light 35 positioned over the patient's door and to a light and/or audible alarm at a remote nurses' station 38. There are of course a variety of such systems but for purposes of illustration the system described herein, which is one of the more prevalent systems, includes a low voltage power supply 32 for providing power to one leg 23 of the hall light 35 and nurses' call station display 38.

When not powered by a signal from control relay 24, nurses' call station control relay 30 is normally closed to provide a ground path 29, 33 to the hall light 35 and nurses' call station display 38. Ground path 29 is connected to the nurses' call button 31 which has its other lead connected to the ground leg 27 of power supply 32. The other power leg 23 of the power supply is connected to the hall light 35 and nurses' call station display 38. When the control relay 24 sends a signal to control relay 30, relay 30 is opened to break the ground leg 33 to the hall light 35 and nurses' station 38.

Another output of control relay 24 to flasher 28 causes flasher 28 to intermittently operate the flasher relay 40. An intermittent signal from the flasher 28 is passed to an audible alarm 42 which may be in the form of a beeper, voice synthesizer or the like, in the patient's room.

Another normally open output 41 of relay 40 is activated by the relay 40 to provide a ground leg to the nurses' call station 38 and hall light 35. This will provide an intermittent ground because the relay 40 is driven by an intermittent signal from flasher 28. Thus when control relay 24 operates control relay 30 to open the ground leg 33 in the nurses' call light system, the ground to the hall light 35 and nurses' call station 38 is taken up by the intermittent ground on leg 41 from flasher relay 40.

A 12-volt D.C. power supply 46 provides power to all components of the system thus far described except those components of the already existing nurses' call station system which are shown utilizing a 24-volt A.C. power supply 32.

Yet another circuit path 43 from the flasher relay 40 is normally closed to ground out an operating signal to a discreet frequency transmitter 16. When relay 40 operates, the ground leg 43 is intermittently broken to permit transmitter 16 to intermittently operate at its discreet frequency. In order to utilize the radio frequency signal generated by transmitter 16, a remote alarm portion of the system is placed at a central station for remote room monitoring, usually the nurses' station. This remote portion of the system includes a central processing unit 48 which has a receiver for receiving the radio frequency signal from the transmitter 16. The signal from the transmitter 16 is modulated by a programmable modulating device to provide a discreet signal so that each room in which the transmitter 16 is placed may have a discreet signal which is then discernable by the central processing unit 48 to identify the room from which an alarm signal originates. A system produced by Interactive Technologies, Inc., of North St. Paul, Minn., and described as their SX-IVB SECURITY SYSTEM, provides a system including the transmitter 16 and Central Processor thus far described. This system is powered by an 8-volt D.C. power supply 50. The central processor 48 also provides a visual digital readout of a number indicative of the transmitter location originating the discreet alarm signal which is programmed into both the transmitters 16 and the central processor 48. This visual readout would most likely be provided to the nurses' station display 52. In addition, the system utilizes the 110 electrical circuit in the vicinity of the system to provide any number of alarm units such as audible hallway devices 54 which are merely plugged into a wall outlet and which receive a radio frequency signal interposed upon the 110-volt A.C. power supply.

Figure 2:
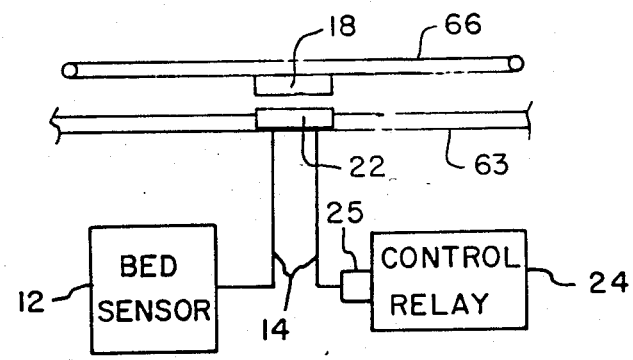
FIG. 2 is a schematic illustration of a bed rail switch for use in the circuit diagram of FIG. 1.

Referring now to FIGS. 2 and 3 of the drawings, a bed rail switch device is shown including a first switch component 18 mounted on a bed rail 66. The first switch component 18 may be a magnet or magnetic device which when positioned near a second switch component 22 such as a magnetic reed switch, will cause the switch to operate. The switch component 22 is a normally closed relay switch which provides a closed circuit path between the bed sensor 12 and the control relay 24. The normally closed state exists when the magnetic switch component 18 is spaced from the stationary component 22. When component 18 is brought into the magnetic proximity of component 22, the switch is opened and in the open position, the relay switch provides a constant signal to the control relay 24 independent of a patient's weight being present to operate the bed sensor. The switch component 22 is mounted on a stationary portion 63 of the frame of the bed 56 so that when the bed rail 66 is in an up position, components 18 and 22 are spaced sufficiently to maintain the relay switch in its normally closed position. When the bed rail 66 is lowered to permit an authorized removal of the patient from the bed, components 18 and 22 are placed in magnetic proximity to operate the switch and thereby provide a constant signal to control relay 24, which simulates the patient's presence in a proper position on the bed. FIG. 3 shows a hospital bed 56 having a mattress 52 positioned over a bed framework including a stationary center frame member 60 and movable hand and foot end portions 62, 64. The bed sensor 12 is shown positioned between the mattress 58 and the stationary center frame member 60. The mattress 58 and the stationary frame member 60 are shown to be separated vertically for purposes of clearly illustrating their relative arrangement on the bed. Their position under actual circumstances is the sensor 12 being sandwiched between the mattress and stationary frame portion 60. A movable bed rail 66 is slideable on vertical supports 68 to raise and lower the bedrail alongside the bed frame and thereby provide in its raised position a means for confining a bed patient to a desired position on the bed, and in its lowered position, permitting the patient to leave the top of the bed area.

Next referring to FIG. 4 of the drawings, the bed sensor 12 is shown in an exploded view and includes an upper plate 70 made of a stiff plastic material such as ⅛ inch thick acrylic plastic or plexiglas. A bottom plate 74 is constructed of a similar acrylic material approximately ¼ inch thick to provide a firm and steady base for the detector assembly. Bottom plate 74 has a drilled opening 71 sized just large enough to pass a pair of conductors 72 which are sealed with a silicon sealant where they pass through opening 71 as will be described later. A pair of ribbon switches 76 are arranged parallel to one another on top of plate 74 and are sandwiched between the top and bottom plates 70, 74 when the detector is assembled. The ribbon switches used herein are manufactured by Tapeswitch Corporation of Farmingdale, N.Y., as 102-BP ribbon switch. This switch is also described in U.S. Pat. No. 2,896,042 entitled "Tape Switch", which was issued to R. H. Koenig on July 21, 1959. As shown in FIG. 4, the parallel rows of ribbon switches are electrically connected in parallel to circuit wire 72. The ribbon switches 76 are arranged in the assembly so that their outer edges and ends are spaced inwardly from the outer edges of the top and bottom plates. A configuration that has proven effective is a side spacing "a" of 1½ inches from the edges of the top and bottom plates 70, 74 to the outer edge of the ribbon switches which are each about ½ inch wide. An end spacing "b" of approximately 2" works well. A spacing "c" of about 2¾ inches between the parallel rows of ribbon switches is appropriate for this assembly. The ribbon switches are about .156 inches thick. This switch material is shown in cross sectional detail in FIG. 6, and is comprised of a pair of spaced conductor ribbons which when forced together under pressure to make electrical contact. A cover 78 of polyethylene plastic of approximately 7½ mil thickness and completely sealing the assembly (also see FIG. 5) is next provided to seal the assembly from environmental contamination and to hold the parts of the detector thus far described in assembly. The cover 78 is preferably formed into a bag which closely fits about the assembly so that the assembly can be easily slid into the bag while leaving enough space for the top and bottom plates 70, 74, to move vertically and transversely relative to one another. The end 80 of the bag 78 is then heat sealed to provide a sealed environment within the bag for the assembled detector. This sealed configuration permits the detector to be cleaned with a disinfectant and reused from one patient to another. This reuse procedure is permitted due to the detector being placed below the mattress and also being sealed against fluid contamination. The advent of the discovery of Anti Immune Deficiency Syndrome (AIDS) has caused health care facilities to become extremely cautious regarding the contamination of health care equipment and products which are subjected to the body fluids of patients. Detectors which are placed on top of the mattress under bed clothing are routinely discarded after each patient use. The present detection system is arranged so that its sensitivity and construction features lend it effective for under mattress use, thus removing it from the immediate environment of potential body fluid contamination. In addition, the sealed configuration permits its being cleaned for reuse after each patient turnover. The circuit cord 72 from the ribbon switches 76 passes through a hole in the cover, the hole and cord 72 being again sealed by any good grade of silicon sealant. FIG. 4 also shows end plates 84 which are made from a thin tough material such as 0.03 inch acrylic plastic. The end plates 84 are bonded by glue, epoxy or the like to the bottom outer surface of the cover 78 of the assembly and are positioned at the ends of the assembly. Referring now to FIG. 5, a side angle iron bed frame member 86 is shown having a matrix of wire webbing 88 spanning between the side frame members 86 for supporting a mattress, box springs, or the like in a supple manner. The webbing is attached to the frame by means of coiled spings 90 having their curved ends hooked to the webbing and through spaced holes in the frame members 86. These springs 90 will tend to wear through and rupture the cover 78 of the detector assembly 12. The end plates 84 provide a protective barrier at the ends of the detector assembly 12 so that when the detector assembly is placed on the stationary portion 60 of the bed frame, and lengthwise is dimensioned to lap over the edge of the side frame member 86, the end plates 84 covering that portion of the detector assembly 12 overlying the coil springs 90 will prevent rupture of the environmental sealed cover 78. The stationary center portion 60 of a typical hospital bed frame has a width dimension "e" of approximately 9 inches. The detector assembly 12 has a width dimension "d" of 6¾ inches which approaches the minimum width which is used for the top and bottom detector plates 70, 74. It is preferable to make the detector assembly 12 wide enough so as to fill as much as possible the space occupied by the non-movable center portion 60 of the bed frame. In addition, the length of the detector assembly should be such that it extends onto at least a portion of the frame portion 86 on either side of the bed to give a firm and resistive support to the bottom of the sensor. Such filling of this space with the detector assembly maximizes the detector sensitivity to patient movement. When the detector is placed under the mattress as shown herein, this maximizing of sensitivity becomes even more important because of the attenuating effect of the intervening mattress between the bed patient and the detector.

FIG. 6 of the drawings shows a cross sectional view of the ribbon switch 76 which is used in detector 12. The switch 76 includes an upper ribbon contact 92 which is spaced upwardly from a lower ribbon contact 94, and has an insulating strip 95 which is positioned under the contact 94 and folds over the edges of the lower contact 94 to provide a separating member between the ribbon contacts 92 and 94. The longitudinal edges 96 of the insulating strip 95 are formed in a "Z" shape to provide a spring effect to the separating member for keeping the contacts 92 and 94 from normally coming into contact. The assembly described above is encased in a plastic sheath 97 which transmits force to the contacts 92, 94. Electrical conducting wires 98 are electrically connected to the contacts 92, 94 to provide an electrical indication of when the contacts are spaced or touching. This ribbon switch shown in FIG. 6 is described in detail in U.S. Pat. No. 2,896,042 described above.

In the operation of the system described thus far, reference is first made to FIGS. 2, 3 and 4. When a patient is positioned on the bed mattress 58, enough weight is present on the mattress to sufficiently compress the ribbon switch 76 so that the ribbon contacts 92, 94 therein are electrically connected. The construction of the detector 12, such as size of the detector assembly and these features permitting lateral movement of the top and bottom plates permits patient weight in any number of normal positions on the mattress to provide this contact closing pressure. Thus, the circuit path 14 is closed when a patient is positioned on the bed. This in turn provides a holding voltage to the control relay 24 to hold the relay in a deactivated or open state. A capacitive delay circuit is connected across the coil of the relay to provide a delay of approximately .2 seconds so that momentary opening of the ribbon switch contacts due to a patient shifting positions, will not set off the alarm system. In this deactivated state the control relay passes a power signal to the LED 26 to provide a visual signal to health care workers in the room that the system is activated and ready to operate. When patient weight is removed from the detector 12, a movement signal is passed by the control relay to the nurses' call station relay 30. Activation of relay 30 opens a ground leg circuit path passing from the power supply 32 through the patient operated call button 31 and relay 30 to the nurses' hall light 35 and nurses' call station display 38. This in turn disables the normal operation of the nurses' call station call button 31, so that if this system is being operated by the patient's button 31, it is disabled by the patient trying to move from the bed. At the same time another output of control relay 24 drives the flasher 28 to generate an intermittent signal to operate flasher relay 40 in an intermittent fashion. Operation of flasher relay 40 provides an intermittent alternative ground path 41 to the hall light 34 and nurses' call station display 38 to cause their intermittent operation. In addition, if the patient bed monitor portion of the system should fail, such as by power failure, the nurses' control relay 30 which is normally closed, will remain normally closed in the absence of a movement signal from control relay 24. The circuit path from control relay 24 is normally open absent a movement signal from the bed sensor which closes the relay for sending out a control signal to flasher 28 and nurses' call station relay 30. When flasher 28 signal operates the flasher relay 40, an intermittent signal is also passed to audible alarm 42 which provides a signal within the normal audible range of a patient to let the patient know that he has caused an alarm by his movement which in many cases will remind the patient that he/she is exceeding the desired movement range and thereby encourage the patient to return to the desired position on the bed. One such audible alarm is a voice synthesizer which would speak a phrase such as "Please return to your bed" or the like so that if the patient in fact is getting out of bed, they will be encouraged to return. Another output 43 of the flasher relay 40 operates a transmitter 16 which outputs, on an intermittent basis, a discreet frequency RF signal that is modulated so as to provide a discreet signal that is different for each transmitter 16 in a particular hospital system. A remote receiver for the transmitter's discreet signal is housed in a central processing unit 48 which is located at a central monitoring station such as a nurses' station. The central processing unit 48 has a visual display readout that identifies the location of a transmitter being activated by undesired patient movement. The central processor 48 also provides an output signal that can be used to operate a remote alarm 54 in the hospital corridors for example. In the system shown in FIG. 1, the bed sensor output passes through circuit path 14 through a quick disconnect jack 25 to the control relay 24. The control relay is in a normally open state until the circuit path 14 is opened by the patient lifting their weight from the detector 12 for a sufficient time to overcome a capacitive delay circuit across the coil of control relay 24. The delay circuit causes the relay 24 to delay about 0.2 of a second before being activated to provide a power signal output to the nurses' call station relay 30. When relay 30 is activated it breaks a grounding leg to the nurses' call station and hall light as described above with respect to FIG. 1. Operation of relay 24 also shuts off the power to LED 26. This would always tell a staff person that the system is either not operating or that patient's weight is not closing the detector 12. If it is desired to move the patient from their bed, the circuit path 14 is opened by removing a male jack end of circuit path 14 from a female connector in quick disconnect jack 25. A jack switch, not shown, closes to simulate a closed circuit path 14 which is the condition existing when a patient is on the bed over the detector 12. Thus the system's alarms are not activated.

An alternative system is shown in FIG. 2 for connecting the bed sensor circuit path 14 to the control relay. As described with respect to FIG. 2, a magnetically operated switch is interposed in the circuit path 14, with the switch having a stationary switch component 22 mounted on the bed frame 63 and a proximity switch component 18 mounted on the bed rail 66. When the bed rail is raised to confine the patient to the bed area, the switch components 18, 22 are spaced so that the relay switch component 22 remains in a normally closed condition to close the circuit path 14 with the sensor 12 included in the circuit. When the bed rail is lowered, the magnetic component 18 of the switch is brought into magnetic proximity of the magnetically activated switch component 22 to operate the switch 22. When operated, switch 22 maintains a constant power signal to the control relay 24 which disables the detector 12 from the circuit and in effect simulates the presence of a person in the bed in a proper position to avoid the actuation of any alarm systems when the bed rail is down. In this manner when a patient is removed from the bed by lowering the bed rail, the system will not sound any alarms and when the patient is repositioned on the bed surface and the rail is again raised, the system is once again operable with the detector 12 in series in the circuit path 14.

It is readily seen that there are any number of combinations of alarm schemes that might be utilized in a health care facility since each facility of course has its own set of criteria that must be accommodated to provide a workable system. It is the purpose of this system to provide a detection device that is safe and reliable and a system for providing alarms that will maximize the probability of avoiding the unauthorized patient movement from their beds. This system provides the flexibility necessary to carry out these purposes.

While particular embodiments of the present invention have been shown and described, it is apparent that changes and modifications may be made without departing from this invention in its broader aspects and therefore the aim in the appended claims is to cover all such changes and modifications as fall within the true spirit and scope of this invention.

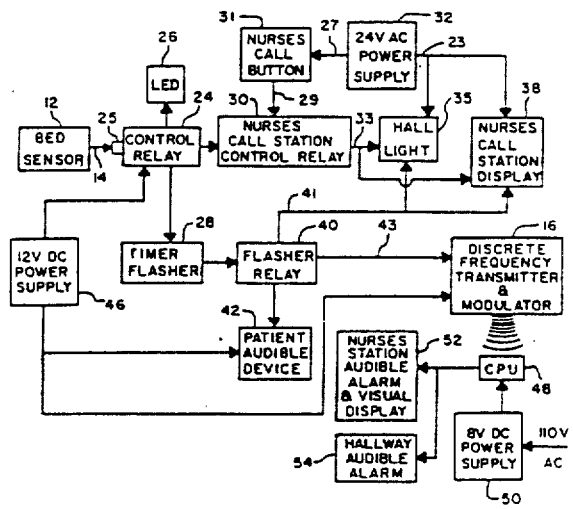

What is claimed is:

1. In a confined bed patient alarm system for use in conjunction with a call alarm system having signal means operable by a patient to provide a first alarm signal to a call alarm device in a first mode circuit, apparatus means for providing a second alarm signal to the call alarm to operate the call alarm in a second mode distinguishable from the first mode, which circuit apparatus means comprises:

Means for detecting a parameter indicative of patient movement;

Control means responsive to said detecting means for supplying a movement signal indicative of such movement;

Means responsive to such movement signal for deactivating the signal means operable by a patient to operate the call alarm device in the first mode; and Means responsive to such movement signal for providing a second alarm signal to operate the call alarm device in the second mode distinguishable from the first mode.

2. The apparatus of claim 1 wherein the call alarm device is a nurses' call alarm which when operated in the first mode presents a steady alarm signal and further wherein said means for providing a second alarm signal includes means for providing an intermittent signal to the call alarm to provide an intermittent alarm signal in the second mode.

3. The apparatus of claim 1 wherein the call alarm has a power source independent of the deactivating means and further wherein said deactivating means includes normally closed switch means for providing a circuit path for said first alarm signal in the absence of a movement signal and operable in response to a movement signal for opening the normally closed switch means so that if said deactivating means loses its power supply, said call alarm device is operable by said first alarm signal.

4. The apparatus of claim 1 wherein said detecting means includes a pressure sensitive switch device which is normally in a closed state and said control means is operable when said switch device is in an open state.

5. The apparatus of claim 4 wherein said switch device is normally held in a closed state by the weight of a patient's body positioned on a bed.

6. The apparatus of claim 4 wherein said switch device is in the form of a ribbon switch which is positioned under the bed's mattress transversely across the bed frame approximately midway between the ends of the bed directly beneath the place where the patient's hips would normally be positioned.

7. The apparatus of claim 4 wherein said control means is in an unoperated state when said switch device is closed and further including circuit wire means between said detecting means and said control means for carrying a signal from said detecting means to said control means to maintain said control means in an unoperated state; conveniently operable connect means on said control means for providing a means for quickly connecting and disconnecting the circuit wire means to said control means, and means on said connect means for providing a signal for maintaining said control means in an unoperated state when said circuit wire means is disconnected from said control means.

8. The apparatus of claim 7 and further including visible signal means operable in response to said control means being in an inoperable state.

9. The apparatus of claim 1 and further including remote alarm means operable in response to a discreet radio frequency signal; and means responsive to the operation of said control means for providing a discrete radio frequency signal to operate said remote alarm means.

10. The apparatus of claim 2 and further including audible alarm means within the normal hearing range of the bed patient and second control means operable in response to said intermittent signal means for operating said audible alarm means, said audible alarm means being unaffected by the operation of said first alarm signal.

11. The apparatus of claim 10 and further including remote alarm means operable in response to a discreet radio frequency signal: and transmitter means operable in response to the operation of said second control means for operating said remote alarm means.

12. The apparatus of claim 11 wherein said transmitter means is conveniently programmable to operate at any one of a plurality of discreet frequencies so that the patient alarm system can be provided for a plurality of confined bed patients each having a discreet frequency assigned to permit identification of the bed patient originating the second alarm signal.

13. The apparatus of claim 2 and further including remote alarm means operable in response to a discreet radio frequency signal; second control means operable in response to said intermittent signal means; and transmitter means operable in response to the operation of said second control means for operating said remote alarm means.

14. The apparatus of claim 13 wherein said remote alarm means includes central processing unit means including means for providing visible indicia related to and indicative of said discreet radio frequency signal; first audible alarm signal means at the location of said central processing unit means; means remote from said central processing unit means for providing a second audible alarm signal, said first and second audible alarm means being operable in response to the reception of a discreet radio frequency signal at the location of said central processing unit means.

15. The apparatus of claim 1 wherein the patient's bed is equipped with a bed rail movable between first and second fixed positions, and further including bed mounted switch means having a first switch component mounted on said bed rail and movable therewith between first and second fixed positions, and a second switch component mounted on said bed so as not to move with the bed rail, said first switch component being connected by means of a circuit path with said detecting means and said second switch component being connected by means of a circuit path with said control means whereby when said bed rail is in one of said first and second fixed positions, said switch means is operative to close a circuit path between said detecting means and said control means and when said bed rail is in the other of said first and second fixed positions, said switch means is operative to open the circuit path between the detecting means and said control means.

16. The apparatus of claim 15 wherein said first switch component of said switch means is a magnetically operable switch operable to open and close in response to the occurrence of a magnetic field in close proximity to said switch, and wherein said second switch component is means for providing a magnetic field.

17. In a bed patient alarm system for use with a bed having a bed rail movable between up and down positions, whereby a detection device is positioned on the bed to provide a signal indicating the movement of a patient from the patient's normal position on the bed, means for permitting the patient to move from such normal position when the bed rail is down without activating the alarm system, which means comprises:

Control means connected to a circuit path and operable to provide an alarm when activated by a signal applied to said circuit path;

Switch means mounted on the bed and having a first component positioned on the bed so as not to move with the bed rail and a second component positioned on the bed so as to move with the bed rail, said first component being connected by a circuit path with the detection device on the bed and said second component being connected to said control means circuit path, said first and second components arranged so that when the bed rail is in an up position to form an enclosure to keep a patient in the bed, the first and second switch components are arranged to provide a closed circuit path between the detection device and the control means and when the bed rail is in a down position to permit the patient to more easily move from the bed, the first and second switch components are arranged to open the circuit path between the detection device and the control means.

18. The apparatus of claim 17 wherein said first component is a device for generating a magnetic field and said second component is a switch element activated by the proximity of a magnetic field to form a circuit path through the switch means.

19. The apparatus of claim 17 and further including means operable in response to the closing of the circuit path between the detection device and the control means for providing an intermittent signal, and means operable in response to said intermittent signal for providing an alarm perceivable by a bed patient in the proximity of the bed position.

20. The apparatus of claim 17 and further including visual indicator means operable to provide a visual signal when said circuit path between the detection device and said control means is closed.

21. The apparatus of claim 17 wherein said detection device includes pressure sensitive means responsive to pressure developed by the weight of a patient positioned in the normal patient position for maintaining a circuit path closed.

22. The apparatus of claim 21 wherein the detection device further includes a ribbon switch means having first and second elongated electrically conductive members lying in a parallel spaced configuration one above the other, and means for normally maintaining the space between the first and second members to prevent an electrical contact between the members, such means for maintaining such space between said electrically conductive members being responsive to the application of pressure to one of said elongated members to move against the other elongated member to form an electrically conductive path.

23. The apparatus of claim 22 wherein the detection device is designed for use with a bed having a mattress arranged over a transverse matrix of webbing attached to the bed frame by coiled springs and wherein the bed has movable end portions which are pivoted to raise and lower and are separated by a center transverse section that is normally stationary, and further including a bottom plate sized for positioning transversely across the normally stationary portion of the bed with its ends positioned over the bed frame and its center portion positioned over the webbing matrix; a top plate sized to matingly be positioned over the bottom plate and having said ribbon switch means positioned between said top and bottom plate, said top plate being arranged for positioning under a mattress on the bed.

24. The apparatus of claim 23 and further including cover means positioned about said top and bottom plates to maintain said top and bottom plates in assembly about said ribbon switch means while permitting relative movement between said plates in both a transverse and longitudinal plane.

25. The apparatus of claim 23 wherein said top and bottom plates are separated only by said ribbon switch means said ribbon switch means being arranged in two elements comprised of side by side spaced parallel rows with the edges of said elements being set inwardly from the edges of said top and bottom plates so that if placed under sufficient compressive force the edges of such top and bottom plates could be brought into contact.

26. The apparatus of claim 23 and further wherein said cover means is sealed about the assembly of said top and bottom plates with the ribbon switch means sandwiched therebetween, and means for providing a sealed access for the circuit path between said detection device and said first component.

27. The apparatus of claim 24 wherein said cover means is a pliable material substantially capable of being sealed against the intrusion of moisture and further including end members positioned over the bottom surface of the outer cover means at each end of said assembly for preventing said cover means from being ruptured by the coil springs connecting the webbing matrix of the mattress to the bed frame.

28. Switch apparatus for use in a bed patient alarm system utilizing a hospital type bed having end sections movable to adjust the contour of the bed and having a stationary transverse portion in the mid section of the bed frame approximate to where the hips of a person reclining on the bed would be positioned, overlain by a mattress, comprising:
upper and lower plate means formed of substantially rectangular rigid plate members having an elongated configuration sized to be positioned on and take up a substantial portion of the stationary transverse portion of the bed;
ribbon switch means sandwiched in assembly between said upper and lower plate means, said upper and lower plate members being free to move back and forth toward one another while compressing said ribbon switch means therebetween and being free to move transversely relative to one another in all directions in the plane of the upper and lower plate means: and cover means for holding the plate means and switch means in assembly.

29. The apparatus of claim 28 wherein said cover means for holding said upper and lower plate members in relatively movable assembly is also arranged to prevent contaminants from entering into the assembly from the area of the bed.

30. The apparatus of claim 29 wherein said cover means is comprised of a heat sealable pliable plastic material of sufficient thickness to provide an environmentally sealed configuration when subjected to use beneath a bed mattress while resting on a bed frame, while readily transmitting pressure applied to a mattress by the weight of a bed patient to the upper plate member.

31. The apparatus of claim 29 and further including a alarm means operable in response to signals transmitted through an electrical circuit path and electrical circuit path means connected between said alarm means and said ribbon switch.

32. The apparatus of claim 31 and further including sealed access means in said cover means for providing an environmentally sealed electrical path access way for a circuit path connected between said alarm means and said ribbon switch.

33. The apparatus of claim 31 wherein said hospital type bed has a bed rail movable between two fixed positions and further including bed mounted switch means having a first switch component mounted on said bed rail and movable therewith between first and second fixed positions; and a second switch component mounted on said bed so as not to move with the bed rail, said first switch component being connected by a circuit path with said ribbon switch and said second switch component being connected by a circuit path with said alarm means.

34. The apparatus of claim 28 wherein said ribbon switch means is comprised of two rows of electrically connected ribbon switches which are arranged in side by side parallel configuration with the laterally outwardly facing ends and sides of the rows of ribbon switches being spaced inwardly from the outer edges of the upper and lower plate means.

35. The apparatus of claim 29 and further including cover means positioned over the bottom end surfaces of said cover means to protect said cover means from being ruptured by contact with the bed frame.

* * * * *

UNITED STATES PATENT AND TRADEMARK OFFICE
CERTIFICATE OF CORRECTION

PATENT NO. : 4,907,845

DATED : March 13, 1990

INVENTOR(S) : Wood

It is certified that error appears in the above-identified patent and that said Letters Patent is hereby corrected as shown below:

The title page should be deleted to appear as per attached title page.

Signed and Sealed this

Twenty-fifth Day of December, 1990

Attest:

HARRY F. MANBECK, JR.

*Attesting Officer*         *Commissioner of Patents and Trademarks*

United States Patent [19]

Wood

[11] Patent Number: 4,907,845
[45] Date of Patent: Mar. 13, 1990

[54] BED PATIENT MONITORING SYSTEM

[76] Inventor: Ron Wood, P.O. Box 35446, Tulsa, Okla. 74153

[21] Appl. No.: 245,227

[22] Filed: Sep. 16, 1988

[51] Int. Cl.⁴ .............................................. G08B 23/00
[52] U.S. Cl. ................................. 340/573; 200/85 R
[58] Field of Search ................ 340/573, 666, 686; 200/85 R

[56] References Cited

U.S. PATENT DOCUMENTS

| | | | |
|---|---|---|---|
| 4,179,692 | 12/1979 | Vance | 340/573 |
| 4,228,426 | 10/1980 | Roberts | 340/573 |
| 4,446,345 | 1/1984 | Sheiry | 200/85 R |
| 4,484,043 | 11/1984 | Musick et al. | 200/85 R |
| 4,539,560 | 9/1985 | Fleck et al. | 340/573 |
| 4,633,237 | 12/1986 | Tucknott | 340/573 |
| 4,638,307 | 1/1987 | Swartout | 340/666 |
| 4,658,242 | 4/1987 | Zeder | 340/693 |
| 4,661,664 | 12/1985 | Miller | 340/666 |

Primary Examiner—Reinhard J. Eisenzopf
Assistant Examiner—Maura K. Regan

[57] ABSTRACT

A system is shown for detecting the movements of a patient confined to a bed so as to determine if there is the likihood that the patient is trying to leave the bed. A sensor is arranged to be placed under the mattress of a bed next to the frame and is totally sealed from the intrusion of contaminants so that it is not necessary to discard the sensor after a patient is discharged. The sensor utilizes ribbon switches sandwiched in assembly between stiff plexiglas plates. The assembly is sealed in a bag that holds the parts in assembly while permitting relative movement in all directions. The alarm system is arranged so that if the sensor detects undesired patient movement, the regular nurses' call light system is deactivated and an alarm distinguishable therefrom is superimposed on the nurses' call light alarm. In addition, an alarm audible to the patient encourages the patient to return to the desired position on the bed. The system then returns to normal and the alarms cease so that resetting is not necessary. Other alarms are activated at remote locations. A bed rail activated switch is utilized to arm and disarm the system so that if the bed rail is lowered to remove a patient from the bed, the alarms are not activated and when a patient is replaced on the bed and the rail is raised, the system is reactivated.

35 Claims, 2 Drawing Sheets